(12) United States Patent
Von Lilienfeld-Toal et al.

(10) Patent No.: US 11,391,703 B2
(45) Date of Patent: Jul. 19, 2022

(54) PHOTO-ACOUSTIC SENSOR HEAD AND PHOTO-ACOUSTIC MEASURING APPARATUS WITH IMPROVED INTERFERENCE SIGNAL SUPPRESSION

(71) Applicant: QUANTUNE TECHNOLOGIES GMBH, Berlin (DE)

(72) Inventors: Hermann Von Lilienfeld-Toal, Gelnhausen (DE); Jan-Ferenc Kischkat, Berlin (DE); Oliver Supplie, Berlin (DE)

(73) Assignee: QUANTUNE TECHNOLOGIES GMBH, Berlin (DE)

( * ) Notice: Subject to any disclaimer, the term of this patent is extended or adjusted under 35 U.S.C. 154(b) by 186 days.

(21) Appl. No.: 16/756,164

(22) PCT Filed: Oct. 26, 2018

(86) PCT No.: PCT/EP2018/079397
§ 371 (c)(1),
(2) Date: Apr. 15, 2020

(87) PCT Pub. No.: WO2019/081701
PCT Pub. Date: May 2, 2019

(65) Prior Publication Data
US 2020/0333296 A1 Oct. 22, 2020

(30) Foreign Application Priority Data

Oct. 27, 2017 (DE) ..................... 10 2017 219 338.7

(51) Int. Cl.
*G01N 29/22* (2006.01)
*G01N 29/24* (2006.01)

(52) U.S. Cl.
CPC ....... *G01N 29/2418* (2013.01); *G01N 29/221* (2013.01)

(58) Field of Classification Search
CPC ........... G01N 29/2418; G01N 21/1702; G01N 29/2221; G01N 2021/1757; A61B 5/0095; A61B 5/4845; A61B 5/14532
(Continued)

(56) References Cited

U.S. PATENT DOCUMENTS 9,453,761 B2 9/2016 Ida
2010/0053618 A1 3/2010 Nakajima et al.
(Continued)

FOREIGN PATENT DOCUMENTS

| JP | 2017-046826 | 3/2017 | | |
|---|---|---|---|---|
| WO | WO-2012077356 A1 | * | 6/2012 | ........... A61B 5/0095 |
| WO | WO-2015174085 A1 | * | 11/2015 | ........... A61B 5/0095 |

OTHER PUBLICATIONS

Schmid et al. "Photoacoustic absorption spectra of biofilms," Review of Scientific Instruments, Jan. 2003, vol. 74, No. 1, pp. 755-757.
(Continued)

*Primary Examiner* — Jacques M Saint Surin
(74) *Attorney, Agent, or Firm* — Sheridan Ross P.C.

(57) ABSTRACT

The disclosure relates to a photoacoustic sensor head for detecting acoustic signals which are excited in a sample by absorption of pulsed measuring light, comprising a contact prism which is transparent for the measuring light and has a sample contact surface, a detection surface arranged opposite the sample contact surface and a light entrance surface arranged adjacent to the detection surface, as well as means for radiating the measuring light through the light entrance surface in the direction of the sample contact surface, wherein a detection device comprising at least one sound transducer is arranged in a manner covering the detection surface, characterized in that those portions of the measuring light which are reflected at the sample contact surface are directed to the detection surface or to the light entrance surface, wherein a material layer containing a material
(Continued)

Figure 1:
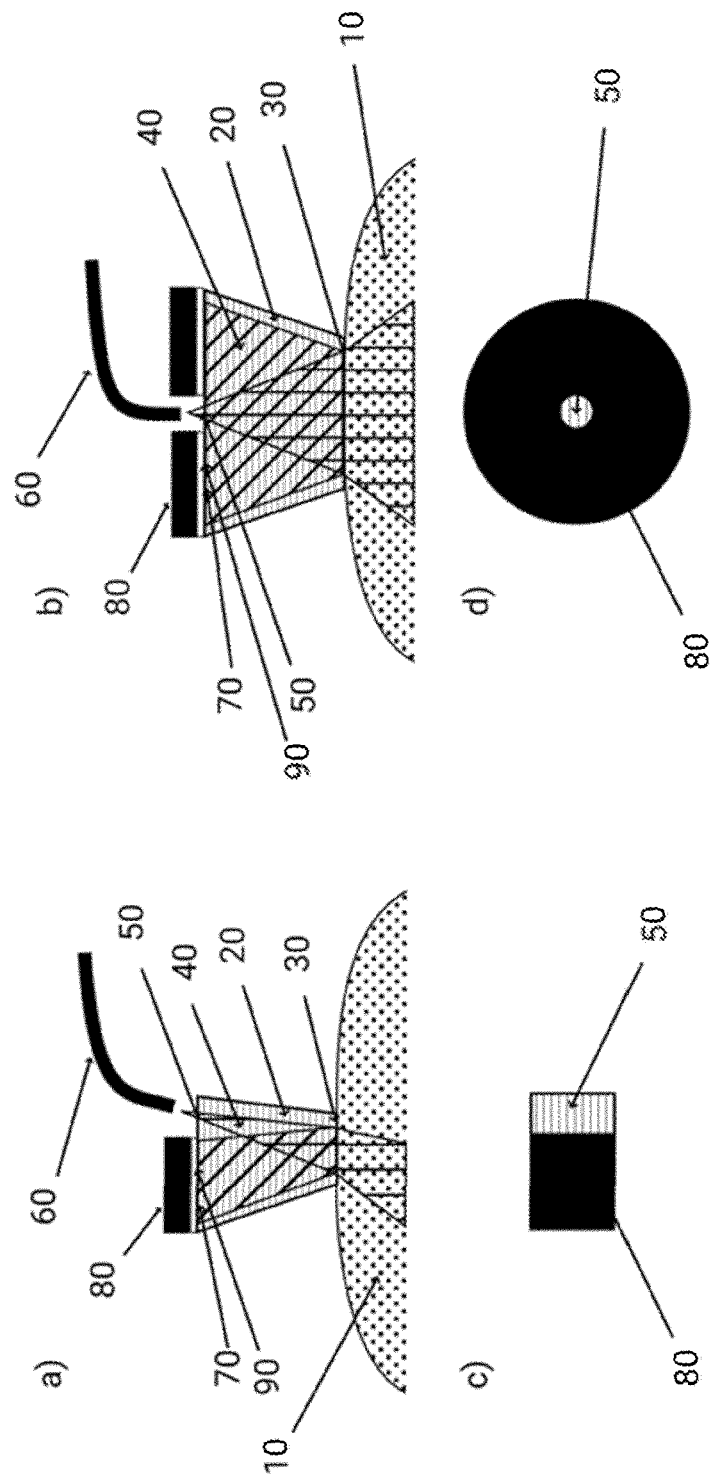

which absorbs the measuring light is arranged between the detection surface and the detection device.

12 Claims, 2 Drawing Sheets

(58) Field of Classification Search
USPC .......................................................... 73/601
See application file for complete search history.

(56) References Cited

U.S. PATENT DOCUMENTS

| | | |
|---|---|---|
| 2010/0094134 A1 | 4/2010 | Zhu et al. |
| 2011/0112391 A1 | 5/2011 | Nishihara et al. |
| 2012/0329904 A1* | 12/2012 | Suita ...................... C08K 3/013 |
| | | 523/105 |
| 2013/0144149 A1* | 6/2013 | Luo ...................... A61B 5/0095 |
| | | 600/407 |
| 2014/0066743 A1 | 3/2014 | Nakajima et al. |
| 2014/0307259 A1* | 10/2014 | Ida ...................... G01N 21/1702 |
| | | 356/432 |
| 2016/0220120 A1* | 8/2016 | Kim ...................... A61B 5/0066 |
| 2018/0263500 A1 | 9/2018 | Shigeta |

OTHER PUBLICATIONS

Translated International Search Report for International (PCT) Patent Application No. PCT/EP2018/079397, dated Jan. 30, 2019, 3 pages.

* cited by examiner

PHOTO-ACOUSTIC SENSOR HEAD AND PHOTO-ACOUSTIC MEASURING APPARATUS WITH IMPROVED INTERFERENCE SIGNAL SUPPRESSION

CROSS REFERENCE TO RELATED APPLICATIONS

This application is a national stage application under 35 U.S.C. 371 and claims the benefit of PCT Application No. PCT/EP2018/079397 having an international filing date of 26 Oct. 2018, which designated the United States, which PCT application claimed the benefit of German Patent Application No. 10 2017 219 338.7 filed 27 Oct. 2017, the disclosures of each of which are incorporated herein by reference in their entireties.

The invention relates to a photo-acoustic sensor head for the detection of acoustic signals, which are triggered in a sample through absorption of a pulsed measuring light, comprising a contact prism transparent for the measuring light with a sample contact surface, a detection surface arranged opposite the sample contact surface and a light entry surface arranged adjacently to the detection surface as well as means for irradiating the measuring light through the light entry surface in direction of the sample contact surface, wherein a detection device comprising at least one sound converter is arranged so as to cover the detection surface.

The invention further relates to a photo-acoustic measuring apparatus comprising a previously mentioned photo-acoustic sensor head, a light source for pulsed measuring light, a device for supplying the measuring light to the sensor head, a device for measured data recording by the detection device and a device for lighting control, which causes the light source to emit measuring light pulses of a predetermined pulse duration at predetermined points in time.

Photo-acoustic measuring apparatuses and sensors are known means for detecting and quantifying substances utilising their characteristic light absorption. In order to examine a sample for a searched-for substance, the sample is illuminated with a measuring light, which comprises one or more light wavelengths, which are already known as characteristic absorption wavelengths of the substance. The measuring light is irradiated into the sample in a pulsed manner and absorbed there to a locally varying degree of strength in dependence of the distribution of the substance. The energy imported through the light absorption causes the sample to heat up and thermo-mechanically expand. Both trigger relaxation processes, which distribute the inhomogenously imported energy across the sample, in order to re-establish the equilibrium. This takes effect via heat diffusion and the propagation of pressure waves—sound waves—through the sample, towards a. o. the sample surface.

In the present invention the acoustic signal generated through light absorption in the sample is detected and evaluated. To this end a photo-acoustic sensor head is provided which is in mechanical contact with a sample surface. The sensor head comprises a sample contact surface provided for this contact, which as a rule is designed as a planar surface. The sensor head consists of a rigid solid material, such as glass or a hardened plastic, and is able to at least partially receive a sound wave generated in the sample and arriving at the sample contact surface and guide it through the solid material to a sensor head external surface opposite the sample contact surface, which is denoted as detection surface. A detection device is arranged on the detection surface which comprises at least one sound converter, which detects the sound wave arriving there. Commonly used sound converters are manufactured from a piezo-electric material and convert pressure fluctuations directly into electric signals.

Photo-acoustic measurements are used to determine the composition of fluids, gases and solid bodies in a non-invasive and non-destructive manner. They are also in common use in medical diagnostics, wherein the sensor head is brought into the contact with the human body, be it inside the body or on the skin. Possible measuring applications occur above all in the field of determining, in a non-injuring manner, blood content substances such as drugs and alcohol or even blood sugar.

The normal measurement variables for photo-acoustic measuring are the amplitudes of the arriving acoustic signals and the times of arrival. From these the response of the sample can be reconstructed also as regards partial volumes of the sample, e.g. voxels, so that conclusions can be drawn as regards the quantitative distribution of absorbing substances. Moreover the measuring light may originate from a tuneable light source such as a laser and encompass a spectral range. Individual measuring light pulses may span different portions of the spectral range respectively and also trigger acoustic signals in dependence of the wavelength. This permits analysing a number of or all substances in a sample using the same measurement.

In order to detect substances near the sample surface it is important to arrange the sample contact surface, at which the acoustic signal generated in the sample shall be taken, in the immediate vicinity of the sample surface illuminated by measuring light. In particular the sensor head may comprise a solid material body, the so-called contact prism, which is transparent for the measuring light. The contact prism may further comprise a light entry surface opposite the sample contact surface and permeable for the measuring light as well as means arranged there, in order to irradiate the measuring light into the contact prism in the direction of the sample contact surface. Such means may for example comprise an optical fibre fastened with glass solder to the light entry surface. Irradiating through the contact prism onto the sample contact surface allows an acoustic response to be reliably created and detected in the sample regions directly existing below the sample contact surface.

It is known in the art to design the contact prism and the means for irradiating the measuring light in such a way that the measuring light illuminates the entire sample contact surface. It is also common practice to design the detection device comprising at least one sound converter in such a way that it covers the entire detection surface of the contact prism. This is meant to ensure that all acoustic signals which reach the detection surface are detected. It is possible, though not mandatory, that the detection device also comprises an array of sound converters, which are arranged next to each other on the detection surface.

With photo-acoustic measuring according to the state of the art a multitude of measuring light pulses are irradiated into the sample and the electric signals of the detection device are selectively amplified with a lock-in amplifier, which is tuned to the repetition rate of the measuring light pulses in order to improve the signal noise ratio (SNR).

Signal portions not originating in the sample but occurring exactly at the same repetition rate as the measuring light pulses can, however, not be effectively suppressed in this way. In the first place such signal portions result from the reflection of a portion of the measuring light at the sample contact surface, whereupon this measuring light portion is partially reflected and partially absorbed at inner surfaces of the contact prism and at structural elements of the sensor head, including the detection device, which can lead to interfering acoustic inputs at several points of the sensor head. This interfering acoustic signal develops practically immediately during irradiation of a measuring light pulse, but—in particular also for sound reflections within the contact prism—comprises a broad interval of sound travel times until it reaches the detection device, where it is then detected superimposed by the useful acoustic signal of the sample.

The interference signal caused by the apparatus has the same relationship to the measuring light pulses as the useful signal and can therefore not be removed by lock-in amplification.

The U.S. Pat. No. 9,453,761 B2 by IDA describes an approach to temporally separate interference signals caused by the apparatus from useful signals by designing the sensor head in an appropriate manner. To this end IDA provides for the detection device to be arranged at a larger distance from the sample than the exit end of a fibre, from which the measuring light enters into the sensor head. In addition a spacer ("arrangement member") permeable to the measuring light is to be arranged between the exit fibre and the sample. IDA alleges that due to this measure a portion of the interference signal ("noise B") can be moved into a time window, which does not start until after the end of recording the useful signal.

The U.S. Pat. No. 9,453,761 B2 makes hardly any mention of the possible sources of the interference signals. In column 4 starting with line 35 of the publication it is alleged that a photo-acoustic wave—a sound wave—is generated in the vicinity of the fibre exit end, then reaches the detection device through reflection at the sample contact surface and there finally causes noise B. This explanation surprises because the material of the contact prism and the measuring light are normally adjusted relative to each other in such a way as to avoid, as far as possible, any absorption of noticeable energy portions during light propagation in the contact prism.

According to a first aspect it is the objective of the invention to propose an improved photo-acoustic sensor head.

According to a second aspect it is the objective of the invention to propose a photo-acoustic measuring apparatus with improved interference signal suppression using the improved photo-acoustic sensor head.

The first objective is met by a photo-acoustic sensor head for the detection of acoustic signals, which are triggered in a sample through absorption of a pulsed measuring light, comprising a contact prism transparent to the measuring light, a detection surface arranged opposite the sample contact surface and a light entry surface arranged adjacently to the detection surface as well as means for irradiating the measuring light through the light entry surface in direction of the sample contact surface, wherein a detection device comprising at least one sound converter is arranged so as to cover the detection surface, characterised in that the portions of measuring light reflected at the sample contact surface are directed at the detection surface or the light entry surface, wherein a material layer containing a measuring-light-absorbing material is arranged between the detection surface and the detection device.

The second objective is met by a photo-acoustic measuring apparatus comprising an inventive photo-acoustic sensor head, a light source for pulsed measuring light, a device for supplying the measuring light to the sensor head, a device for recording the data measured by the detection device and a device for lighting control, which causes the light source to emit measuring light pulses of a predetermined pulse duration at predetermined points in time, characterised in that the measuring apparatus comprises a device for measured data evaluation communicating with the device for lighting control and the device for measured data recording, which causes the device for measured data recording to record the measured data of the detection device only during a plurality of non-overlapping time intervals, the temporal positions of which are predetermined as regards the points in time of emitting the measuring light pulses and the interval lengths of which in total are smaller than the temporal distance between two successive measuring light pulses.

Sub-claims 2 to 5 indicate advantageous designs of the sensor head. Sub-claims 7 to 9 are directed at advantageous designs of the measuring apparatus.

The invention follows the approach by IDA to temporally separate the interference signals from the useful signals. They are then no longer present in the useful signals, i.e. they are suppressed in there.

Starting with the causes mentioned in the beginning for the occurrence of the interference signals caused by the apparatus, the invention pursues the path of removing, as soon as and as completely as possible, that portion of the measuring light from the system, which immediately upon irradiation into the contact prism is incident on the sample contact surface and reflected there into the contact prism.

For this purpose it is provided by the invention to design the contact prism as regards its shape and the arrangement of its side surfaces with respect to each other in such a way that the portions of the measuring light reflected at the sample contact surface are directed at the detection surface or at the light entry surface, in other words, after being reflected once, the light beams reach the detection surface or the light entry surface of the contact prism without any further reflections at internal boundary surfaces and without leaving the contact prism.

The detection surface is covered by the detection device, i.e. the detection device extends across the entire detection surface, and it is advantageously provided under the invention that a material layer containing a measuring-light-absorbing material is arranged between the detection surface and the detection device.

Portions of the measuring light which are incident on the detection surface are, according to invention, absorbed to their fullest possible content, heat up the material layer and trigger a pressure signal, which is immediately detected by the detection unit. The acoustic signal generated in this way is an interference signal of relatively large amplitude, which only occurs during a very short time interval immediately after triggering the measuring light pulse. Useful signals caused by the absorption of the measuring light in the sample must however initially reach the sample contact surface as sound waves, enter the contact prism and pass through the same as far as the detection surface. Accordingly they arrive with a time delay in the magnitude of microseconds. Due to the absorption in the material layer between detection surface and detection device, as forced by the invention, the interference signal is recorded temporally concentrated and separated from the useful signals out of the sample.

Insofar as portions of the measuring light exist which reach the light entry surface, these leave the contact prism at this point. In this case too, the light primarily reflected at the sample contact surface is removed from the measuring system, so that the temporally later occurrence of interference signals is suppressed.

When designing the inventive sensor head the expert has the freedom to determine the shape and size of the sample contact surface and the manner in which he intends to illuminate this with measuring light. Starting with his definitions will then, according to the teaching of this invention, shape and size of the detection surface—and thus at the same time of the detection device and the measuring-light-absorbing material layer—will then be automatically determined by way the expert quite simply taking account of the law of reflection.

In a preferred design of the sensor head the material layer between detection surface and detection device is an adhesive for fastening the detection device to the contact prism. Furthermore it is preferable if the measuring-light-absorbing material is a light-absorber pigment, especially preferably carbon black. Advantageously the pigment may be added separately to a commonly used adhesive.

Furthermore it is regarded as advantageous that the means for irradiating the measuring light comprise at least one optical fibre connected in a manner optically transparent for the measuring light to the light entry surface of the contact prism, wherein the measuring light exiting from the fibre end and thereupon fanning out illuminates the entire sample contact surface. It may be of advantage to provide a plurality of optical fibres next to each other in a linear arrangement for irradiating the measuring light into the contact prism. In this way a sample contact surface extending in parallel to the course of the linear arrangement can be evenly illuminated.

Further, a preferred design of the photo-acoustic sensor head consists in that a backing material is arranged on the at least one sound converter of the detection device, the acoustic impedance of which is greater than that of the sound converter material.

Figure 2:
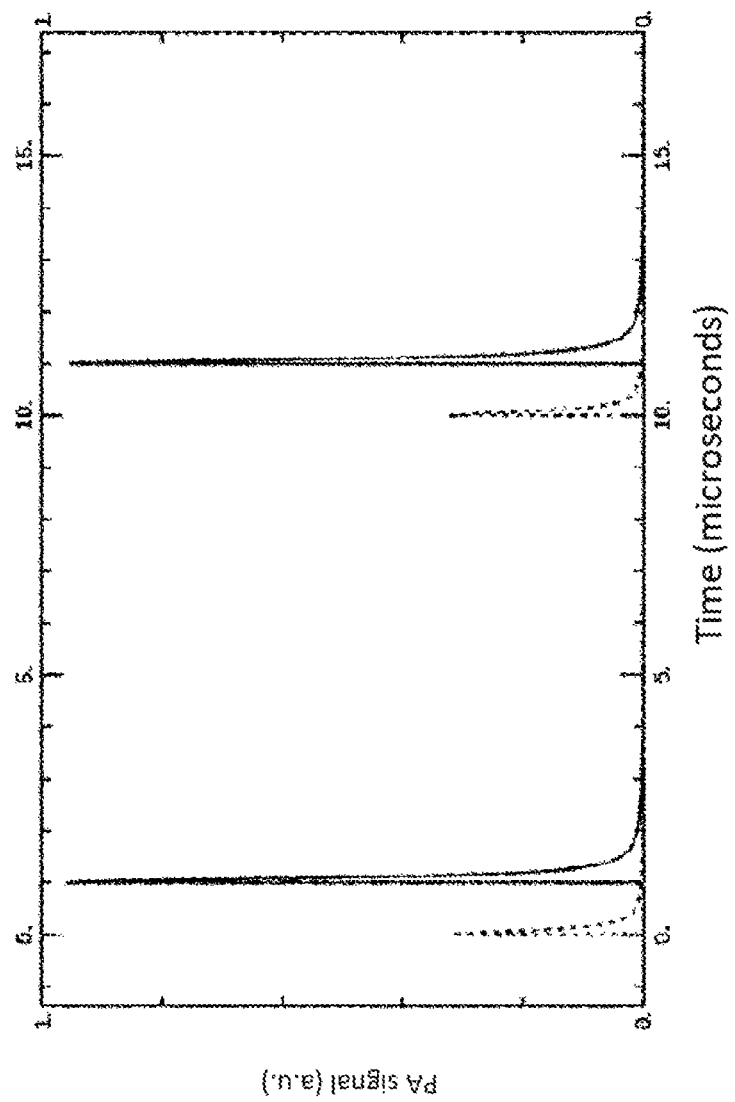

Examples of how the photo-acoustic sensor head could be designed will now be explained in more detail, also with reference to the figures, in which FIG. 1 shows possible designs of the photo-acoustic sensor head in lateral views a) and b) and in top views c) and d);

FIG. 2 shows a schematic plot of the measured pressure amplitudes of the interference signal (broken line) and the useful signal of the sample in the generated temporal separation.

FIG. 1 shows two possible designs of the inventive photo-acoustic sensor head. The part FIGS. 1a) and b) each depict a sample 10, on which a contact prism 20 is arranged such that the sample 10 and the contact prism 20 touch each other at the sample contact surface 30. The material of the contact prism 20 is transparent for the measuring light 40, which is irradiated via at least one optical fibre 60 through the light entry surface 50 into the contact prism 20 in direction of the sample contact surface 30.

Usually the measuring light 40 comprises wavelengths within the infrared spectrum, in particular the near (NIR) and medium infrared (MIR) range. For some purposes however the measuring light 40 may be visible light (VIS) or originate from another non-ionising spectral range.

Due to the transparency request the choice of material of the contact prism 20 orients itself on the wavelengths of the measuring light 40. As regards light in the medium infrared spectrum (MIR) for example, suitable materials are semiconducting materials such as geranium, zinc selenide, silicone, indium phosphide, gallium arsenide or chalcogenide glasses, and as regards light in the near infrared spectrum (NIR) or visible spectrum (VIS) suitable materials are silicone dioxide (quartz, glasses), aluminium oxide (corundum, sapphire, ruby) or even some plastics (e.g. polyethylene).

The means for irradiating the measuring light 40 in the part FIG. 1a) are one or more optical fibres 60, which are arranged fixed to the light entry surface 50 of the contact prism 20. The fixing is not shown. The measuring light 40 exiting from the fibres 60 fans out in the contact prism 20 and illuminates the entire sample contact surface. A first portion of the measuring light 40 penetrates into the sample 10 and triggers useful signals, whereas a second portion of the measuring light 40 is reflected in direction of the detection surface 70. The detection surface 70 is covered by the detection device 80, which comprise at least one sound converter. As a rule the detection device 80 only comprises one single sound converter, which extends across the entire detection surface 70. The detection device 80 is for example glued onto the detection surface 70 of the contact prism 20 by means of the material layer 90, which also contains light absorber particles. The second portion of the measuring light 40 arriving in the material layer 90 is, as far as possible, fully absorbed, which triggers an interference signal. The detection device 80 records the interference signal, before a useful signal from the sample can arrive.

In the design of part FIG. 1b) a small portion of the measuring light 40 is also mirrored back onto the light entry surface 50 and thus into the exit end of the fibre 60. This case is typical if the measuring light 40 is irradiated vertically onto the sample contact surface 30.

The part FIGS. 1c) and d) each show a top view of the sensor heads from the part FIGS. 1a) and b), respectively, wherein the direction of view is onto the sample 10. The light entry surface 50 in FIG. 1c) is formed as a rectangle, so that even a plurality of optical fibres 60 can be arranged and fixed along the long axis of the rectangle. In FIG. 1d) the light entry surface 50 is in the centre of the detection surface 70 with the detection device 80. This configuration too, in which the light entry surface 50 is surrounded by the detection surface 70, is to be understood as adjacent arrangement of the light entry surface 50 to the detection surface 70.

A photo-acoustic measuring apparatus with a photo-acoustic sensor head according to the invention can be designed specifically for advantageous use of the sensor head, in that a measured data evaluation device is added, which takes appropriate account of the isolated interference signal occurring immediately upon irradiating the measuring light 40.

Apart from the sensor head the measuring apparatus comprises a light source for pulsed measuring light 40, a device for supplying the measuring light 40 to the sensor head, a device for measured data recording by the detection device 80 and a device for lighting control, which causes the light source to emit measuring light pulses of predetermined pulse duration at predetermined points in time. Moreover the measuring apparatus shall comprise a device for measured data evaluation communicating with the device for lighting control and the device for measured data recording. The device for measured data evaluation causes the device for measured data recording to record the measured data of the detection device 80 only during a plurality of non-overlapping time intervals, the temporal positions of which are predetermined as regards the points in time of emitting the measuring light pulses and the interval lengths of which in total are smaller than the temporal distance between two successive measuring light pulses.

In other words, the time span between emitting two successive measuring light pulses is divided into non-overlapping time intervals, of which some but not all, are being provided for measured data recording. The device for measured data evaluation specifies the time intervals with data recording after predetermination by the user. For example, the device for measured data evaluation comprises a stop watch which is reset on triggering a measuring light pulse, as well as a table with stop watch readings at which time intervals start and end, in which measured data are to be recorded. In one possible implementation the device for measured data evaluation instructs the device for measured data recording to activate or deactivate data recording when a tabulated stop watch reading is present. The device for data recording comprises at least one non-volatile electronic data memory, which digitally stores the voltage values received from the detection device 80 during the time intervals predetermined for data recording.

Preferably the device for measured data recording and the device for measured data evaluation form a constructional unit. They can be realised in a particularly simple manner by way of programming a conventional personal computer.

In order to remove random noise it is very advantageous to average the recorded measured data across a plurality of measuring light pulses, i.e. across a number of time intervals with respectively the same time reference for emitting a measuring light pulse. Preferably the device for measured data evaluation initiates this process in that it repeats its time requirements directed at the device for measured data across a sequence of measuring light pulses. The recorded measured data can be added up in the data memory of the device for data recording by way of the known boxcar averaging and then divided by the number of measuring light pulses, in order to determine a mean value.

FIG. 2 shows a schematic plot of the temporal course of the pressure amplitude (PA) for two successive measuring light pulses. Random noise has not been taken into account. The solid line curves represent the acoustic useful signal from the sample, which first has to propagate through the contact prism in order to reach the detection device. It therefore arrives distinctly after the interference signal (depicted as a broken line), which is generated immediately after the emission of a measuring light pulse. Both signals can be recorded in separate non-overlapping time intervals. The length of the second time interval (useful signal) can be predetermined by the user; in particular it can be very much larger than the length of the first time interval. Both time intervals together are shorter than the temporal distance between the measuring light pulses.

It appears to be sufficient in many cases and therefore also advantageous that the plurality of time intervals after emission of a measuring light pulse comprises exactly two time intervals. In this case it is preferably provided that the first interval begins at the point in time when the measuring light pulse is emitted, and ends before an acoustic signal generated and entering into the contact prism through the sample contact surface reaches the detection surface.

What is claimed is:

1. A photo-acoustic measuring apparatus, comprising:
   a photo-acoustic sensor head for the detection of acoustic signals that are triggered in a sample through absorption of measuring light, the photo-acoustic sensor head comprising:
   a transparent contact prism with a sample contact surface;
   a detection surface arranged opposite the sample contact surface;
   a light entry surface arranged adjacently to the detection surface;
   a detection device comprising at least one sound converter arranged to cover the detection surface, wherein portions of the measuring light reflected at the sample contact surface are directed at the detection surface or the light entry surface; and
   a material layer containing a material that absorbs the measuring light arranged between the detection surface and the detection device;
   a light source that generates the measuring light;
   a device for supplying the measuring light to the photo-acoustic sensor head;
   a device for measured data recording of the detection device;
   a device for lighting control that causes the light source to emit pulses of the measuring light having a predetermined pulse duration at predetermined points of time; and
   a device for measured data evaluation in communication with the device for lighting control and the device for measured data recording, wherein the device for measured data evaluation causes the device for measured data recording to record the measured data of the detection device only during a plurality of non-overlapping time intervals, wherein temporal positions of the plurality of non-overlapping time intervals are based on the predetermined points in time of the emitted pulses of the measuring light, and wherein interval lengths of the plurality of non-overlapping time intervals in total are smaller than a temporal distance between two successive emitted pulses of the measuring light.

2. The photo-acoustic measuring apparatus according to claim 1, wherein the material layer arranged between the detection surface and the detection device is an adhesive for fastening the detection device to the contact prism.

3. The photo-acoustic measuring apparatus according to claim 1, wherein the material absorbing the measuring light includes a light absorber pigment.

4. The photo-acoustic measuring apparatus according to claim 1, further comprising at least one optical fibre that guides the measuring light to the light entry surface of the contact prism, wherein the measuring light exiting from a fibre end and thereupon fanning out illuminates the entire sample contact surface.

5. The photo-acoustic measuring apparatus according to claim 4, wherein the at least one optical fibre comprises a plurality of optical fibres adjacent to each other in a linear arrangement.

6. The photo-acoustic measuring apparatus according to claim 1, wherein a backing material is arranged on the at least one sound converter of the detection device, wherein an acoustic impedance of the backing material is greater than that of a material of the at least one sound converter.

7. The photo-acoustic measuring apparatus according to claim 1, wherein the device for measured data evaluation causes the recorded measured data to be averaged across a plurality of pulses of the measuring light or performs this averaging.

8. The photo-acoustic measuring apparatus according to claim 7, wherein a time interval starts when the measuring light pulse is emitted and ends before an acoustic signal generated in the sample and entering into the contact prism through the sample contact surface reaches the detection surface.

9. The photo-acoustic measuring apparatus according to claim 7, wherein the plurality of non-overlapping time intervals comprises exactly two time intervals.

10. The photo-acoustic measuring apparatus according to claim 1, wherein the plurality of non-overlapping time intervals comprises exactly two time intervals.

11. A photo-acoustic measuring apparatus, comprising:
a photo-acoustic sensor head for the detection of acoustic signals that are triggered in a sample through absorption of measuring light, the photo-acoustic sensor head comprising:
  a transparent contact prism with a sample contact surface;
  a detection surface arranged opposite the sample contact surface;
  a light entry surface arranged adjacent to the detection surface;
  a detection device comprising at least one sound converter arranged to cover the detection surface, wherein portions of the measuring light reflected at the sample contact surface are directed at the detection surface or the light entry surface; and
  a material layer containing a material that absorbs the measuring light arranged between the detection surface and the detection device;
a light source that generates the measuring light;
a device for supplying the measuring light to the photo-acoustic sensor head;
a device for measured data recording of the detection device;
a device for lighting control that causes the light source to emit pulses of the measuring light having a predetermined pulse duration at predetermined points of time; and
a device for measured data evaluation in communication with the device for lighting control and the device for measured data recording, wherein the device for measured data evaluation causes the device for measured data recording to record the measured data of the detection device only during a plurality of non-overlapping time intervals, wherein temporal positions of the plurality of non-overlapping time intervals are based on the predetermined points in time of the emitted pulses of the measuring light, wherein the device for measured data evaluation causes the recorded measured data to be averaged across a plurality of pulses of the measuring light or performs this averaging.

12. A photo-acoustic measuring apparatus, comprising:
a photo-acoustic sensor head for the detection of acoustic signals that are triggered in a sample through absorption of measuring light, the photo-acoustic sensor head comprising:
  a transparent contact prism with a sample contact surface;
  a detection surface arranged opposite the sample contact surface;
  a light entry surface arranged adjacent to the detection surface;
  a detection device comprising at least one sound converter arranged to cover the detection surface, wherein portions of the measuring light reflected at the sample contact surface are directed at the detection surface or the light entry surface; and
  a material layer containing a material that absorbs the measuring light arranged between the detection surface and the detection device;
a light source that generates the measuring light;
a device for supplying the measuring light to the photo-acoustic sensor head;
a device for measured data recording of the detection device;
a device for lighting control that causes the light source to emit pulses of the measuring light having a predetermined pulse duration at predetermined points of time; and
a device for measured data evaluation in communication with the device for lighting control and the device for measured data recording, wherein the device for measured data evaluation causes the device for measured data recording to record the measured data of the detection device only during a plurality of non-overlapping time intervals, wherein temporal positions of the plurality of non-overlapping time intervals are based on the predetermined points in time of the emitted pulses of the measuring light, wherein the device for measured data evaluation causes the recorded measured data to be averaged across a plurality of pulses of the measuring light or performs this averaging, wherein a time interval starts when the measuring light pulse is emitted and ends before an acoustic signal generated in the sample and entering into the contact prism through the sample contact surface reaches the detection surface.

\* \* \* \* \*